(12) United States Patent
Royer

(10) Patent No.: US 8,231,841 B2
(45) Date of Patent: Jul. 31, 2012

(54) CHROMIUM-FREE INDICATING DEVICE FOR CHLORIDE DETECTION

(75) Inventor: Douglas F. Royer, Gilbert, IA (US)

(73) Assignee: Hach Company, Loveland, CO (US)

( * ) Notice: Subject to any disclaimer, the term of this patent is extended or adjusted under 35 U.S.C. 154(b) by 0 days.

(21) Appl. No.: 13/320,870

(22) PCT Filed: Mar. 1, 2010

(86) PCT No.: PCT/US2010/025798
§ 371 (c)(1),
(2), (4) Date: Nov. 16, 2011

(87) PCT Pub. No.: WO2010/138224
PCT Pub. Date: Dec. 2, 2010

(65) Prior Publication Data
US 2012/0064634 A1     Mar. 15, 2012

Related U.S. Application Data

(60) Provisional application No. 61/182,257, filed on May 29, 2009, provisional application No. 61/219,934, filed on Jun. 24, 2009.

(51) Int. Cl.
*G01N 31/00* (2006.01)

(52) U.S. Cl. ....... 422/420; 422/400; 422/412; 422/68.1; 436/124; 436/810; 205/779; 423/462

(58) Field of Classification Search .................. 422/400, 422/412, 420, 68.1; 436/124, 810; 205/779; 423/462
See application file for complete search history.

(56) References Cited

U.S. PATENT DOCUMENTS

| | | |
|---|---|---|
| 3,510,263 A | 5/1970 | Hach |
| 3,620,677 A | 11/1971 | Morison |
| 3,956,094 A | 5/1976 | Capuano |
| 4,028,197 A | 6/1977 | Capuano |
| 4,211,532 A | 7/1980 | Tobari et al. |
| 4,287,097 A | 9/1981 | Fratzer et al. |
| 4,650,768 A | 3/1987 | Cahill et al. |
| 4,893,108 A | 1/1990 | Kolesar, Jr. |
| 5,229,299 A | 7/1993 | Terry |
| 6,042,543 A | 3/2000 | Warwick et al. |
| 2002/0068016 A1 | 6/2002 | Warner et al. |
| 2003/0165359 A1 | 9/2003 | Chowdhury et al. |
| 2005/0072213 A1* | 4/2005 | Besnard et al. ............. 73/31.06 |
| 2008/0019892 A1 | 1/2008 | Neto et al. |

* cited by examiner

*Primary Examiner* — Jill Warden
*Assistant Examiner* — Monique Cole
(74) *Attorney, Agent, or Firm* — Beusse Wolter Sanks Mora & Maire, P.A.; Mark W. Scott

(57) ABSTRACT

A chemical indicating device (10) for detection of chloride ions in a sample is provided. The chemical indicating device (10) includes a carrier matrix (12) and an indicator (14) having silver and vanadate supported on the carrier matrix (12). A method for detecting chloride ions is also provided.

21 Claims, 3 Drawing Sheets

CHROMIUM-FREE INDICATING DEVICE FOR CHLORIDE DETECTION

The present application, filed Nov. 16, 2011, is a national stage entry of PCT/US10/25798, International Filing Date: Mar. 1, 2010; PCT/US10/25798 Claims Priority from Provisional Application 60/182,257, filed May 29, 2009; and PCT/US10/25798 Claims Priority from Provisional Application 61/219,934, filed Jun. 24, 1009.

FIELD OF THE INVENTION

The present invention relates to an improved chromium-free chemical indicating device and to a chromium-free method for determining the presence and amount of chloride ions in an aqueous sample.

BACKGROUND OF THE INVENTION

The detection of chloride ions is critical for a number of different applications, including but not limited to, health and industrial applications. Numerous indicating devices for the detection of chloride ions are known in the art. The majority of known indicating devices for chloride ions employ a silver chromate or silver dichromate hexavalent chromium (Cr(VI)) compound as the indicating agent, which contains chromium in an oxidation state of +6. Exposure to hexavalent chromium over a prolonged period of time, however, is known to pose significant health risks.

For example, if hexavalent chromium comes into contact with the eyes and skin, hexavalent chromium may cause irritation and even permanent damage if the exposure is long enough. In addition, if hexavalent chromium comes into contact with a cut or laceration on the skin, the compound may cause chrome ulcers, which typically take a long time to heal and may leave a visible scar. If inhaled, hexavalent chromium may irritate the nasal passages, throat, and lungs. Further, prolonged exposure to hexavalent chromium may result in damage to the mucous membranes, nosebleeds, perforation of the septum, and an increased risk of developing lung cancer. Moreover, when exposed to vitamin C in vivo, hexavalent chromium may result in severe damage to the individual's DNA inside the lung's cells. Even further, the International Agency for Research on Cancer (IARC) lists hexavalent chromium as a known human carcinogen.

The Occupational Safety and Health Administration (OSHA) has set acceptable exposure levels for hexavalent chromium in a variety of occupations as follows: 0.005 mg/m$^3$ or 5 micrograms/m$^3$ TWA for General Industry; 0.005 mg/m$^3$ or 5 micrograms/m$^3$ TWA for the Construction Industry; and also 0.005 mg/m$^3$ or 5 micrograms/m$^3$ TWA for the Maritime Industry. Further, the National Institute for Occupational Safety and Health (NIOSH) has deemed 0.001 mg Cr(VI)/m$^3$ 10-hr TWA to be the recommended exposure limit.

In addition to the above concerns, hexavalent chromium-containing devices must also be handled carefully after use and disposed of properly. Hexavalent chromium is prevalent on many environmental lists such as the Resource Conservation and Recovery Act (RCRA) in the United States, the Pollution Release and Transfer Register (PRTR) in Japan, and the European Union Hazardous Waste Directive, for example. While devices and methods that reduce exposure levels of hexavalent chromium may be used, completely eliminating the use of hexavalent chromium in the detection of chloride ions would be more desirable. To date, the known prior art has failed to provide workable, low cost, and readily visible chromium-free indicators and methods for the detection of chloride ions.

BRIEF DESCRIPTION OF THE DRAWINGS

The invention is explained in the following description in view of the drawings that show.

DETAILED DESCRIPTION OF THE INVENTION

Figure 1:
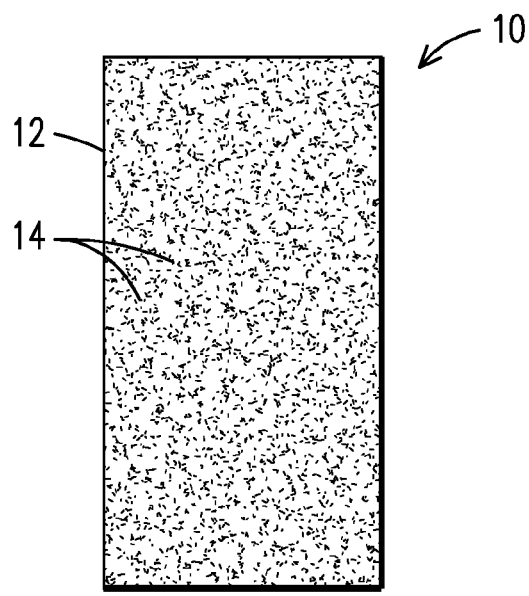
FIG. 1 is a front view of a chemical indicating device in accordance with an aspect of the present invention.

Referring to FIG. 1, there is shown a chemical indicating device 10 (device 10) for the detection of chloride ions in a sample. The device 10 includes at least a carrier matrix 12 and an indicator 14 supported by the carrier matrix 12. Advantageously, the indicator 14 of the present invention is not a hexavalent chromium-based compound as is typical of known indicators for detecting chloride ions. Instead, in the present invention, the indicator 14 comprises a compound having silver and vanadate. In a particular embodiment, the indicator 14 comprises silver decavanadate. The speciation of vanadium into vanadate in aqueous solutions is complex. Specifically, vanadate will undergo self-condensation that is pH dependent. At high pH, vanadate oxoanions exist as $VO_4^{3-}$. As the pH of the aqueous solution drops, $V_2O_7^{4-}$ forms, then $V_4O_{12}^{4-}$, and finally decavanadate $V_{10}O_{28}^{6-}$ (which is an inorganic polymer of vanadate) forms to give a dark orange species. When decavanadate is reacted with a silver-containing compound, silver decavanadate is formed. The silver decavanadate is a precipitate also having very dark orange color. When placed in contact with a chloride ion-containing sample, the dark orange silver decavanadate is easily discolored by the formation of a white precipitate (silver chloride) against the dark orange background. In this way, the device 10 provides a readily observable and measurable colorimetric response in the presence of chloride ions.

Critically, the present inventor has found that compounds comprising silver and vanadate, e.g., silver decavanadate, remain substantially immobilized on the carrier matrix 12 when impregnated therein. By "substantially immobilized," it is meant that enough indicator 14 remains supported on the carrier matrix 12 such that when the carrier matrix is contacted with a sample, a visual determination of the amount of silver chloride precipitated on the carrier matrix 12 can be made against the background of the carrier matrix 12. In addition, by "supported" or "supported on," it is meant that the indicator 14 is sequestered, immobilized, and/or otherwise disposed on a surface of the carrier matrix 12 and/or within the pores of the carrier matrix 12 (if the carrier matrix 12 is a porous carrier matrix as discussed below). At least some degree of immobility of the indicator 14 is critical for the accuracy of the device 10 when placed in contact with a chloride ion-containing sample. If the indicator 14 is washed away from the carrier matrix 12 as the sample moves up the carrier matrix 12, a false positive may result.

In developing a suitable chromium-free indicator, the present inventor has found that while some compounds may provide a colorimetric indication of the presence of chloride ions in a sample, these compounds are typically easily washed off the carrier matrix 12, and thus are not viable options for the indicator 14. The inventor has further surprisingly found that compounds comprising silver and vanadate, e.g., silver decavanadate, are able to remain relatively stationary on different carrier matrices even when the sample is moved along a length of carrier matrices. In one embodiment, the indicator 14 is evenly distributed on the carrier matrix, and in a particular embodiment, the indicator 14 is evenly distributed along an entire length of the carrier matrix.

The carrier matrix 12 may be of any wholly or partially hydrophilic or hydrophobic material. In one embodiment, the carrier matrix 12 comprises a hydrophilic material. It is generally understood that when the carrier matrix comprises a hydrophylic material, the carrier matrix 12 will allow the fluid sample to wick up or flow via capillary action along a length thereof. As the sample travels along the length of the carrier matrix 12, any chloride ions present in the sample will react with the indicator 14 supported on the carrier matrix 12. In another embodiment, the carrier matrix 12 comprises a hydrophobic material. It is generally understood that when the carrier matrix 12 comprises a hydrophobic material, the sample will not easily wick up the carrier matrix 12. Accordingly, in such an embodiment, a syringe, pump, or like device may be used to provide the force necessary to move the sample along a length of the carrier matrix 12.

In addition, the carrier matrix 12 may be a porous material or non-porous material. In one embodiment, the carrier matrix 12 comprises a porous material. In a particular embodiment, the carrier matrix 12 comprises a porous material comprising one or more of a cellulosic material, a glass fiber material, a porous polymeric material, or combinations thereof. With a porous material, it is generally understood that the indicator 14 may be disposed on a surface of the porous material as well as within pores of the porous material. Generally, dipping the carrier matrix 12 in solutions comprising silver and vanadate sources in one or more steps will be sufficient to accomplish the support of the indicator 14 on and within a porous carrier matrix. In another embodiment, the carrier matrix 12 comprises a non-porous material. The indicator 14 may similarly be supported on the non-porous material by dipping the non-porous material in solutions comprising the silver and vanadate sources in one or more steps and thereafter drying the carrier matrix 12.

In one embodiment, the indicator 14 is supported on the carrier matrix 12 via a two dip process for the carrier matrix 12. First, the carrier matrix 12 may be dipped in a first solution comprising a silver source, e.g., silver nitrate, and dried. The carrier matrix 12 may then be dipped in a second solution containing decavanadate. The decavanadate is provided from a vanadate source. After the carrier matrix 12 is dipped in the second solution, the carrier matrix 12 is again dried. The silver from the first solution will react with the vanadate ions in the second solution to produce an orange colored precipitate, e.g., silver decavanadate. The carrier matrix 12 may then cut into strips if desired.

Any suitable vanadate source may be utilized to provide a quantity of vanadate for the indicator 14. The vanadate will be reacted with silver from a silver source to form the indicator 14 in the form of a compound comprising silver and vanadate, e.g., silver decavanadate. As stated above, the speciation of vanadium in aqueous solution is complex. As vanadate self condenses, it is difficult, if not impossible, to distinguish solutions of the same conditions of pH, ionic strength, and vanadium concentration, from different starting materials. Thus, the starting materials for preparing the indicator 14 may be any suitable vanadate source including, but are not limited to, sodium metavanadate, potassium orthovanadate, or vanadium oxide. Decavanadate synthesis, for example, can happen through many routes with many vanadium-based starting materials.

In addition, any suitable silver source may be utilized to provide a quantity of silver for reaction with the vanadate source to form a compound comprising silver and vanadate, e.g., silver decavanadate. In one embodiment, the silver source is a silver salt, e.g., silver nitrate. It will be appreciated by one skilled in the art that the concentration of silver nitrate can vary greatly to accommodate different functional ranges of the device 10. In one embodiment, the amount of vanadium used in the manufacture of the device 10 is in excess of the amount of silver used by at least a 2:1 mole ratio to ensure a complete reaction between the silver and the vanadate. In a particular embodiment, silver decavanadate is produced from silver nitrate and decavanadate according to the following equation:

$$6AgNO_3 + V_{10}O_{28}^{6-} \rightarrow Ag_6V_{10}O_{28} + 6NO_3^-$$ (dark orange)

Optionally, in producing the indicator 14, a suitable drying agent may be added to the components when reacting the silver and vanadate together. In one embodiment, the drying agent is ethanol, which aids in the even drying of the components on the carrier matrix 12.

Since decavanadate in particular forms well at a pH range of 3-6, in one embodiment, the vanadate source may also be provided with an acidifying agent sufficient to adjust the pH of the vanadate source to a pH of 3-6 to encourage the formation of decavanadate. Any suitable compound may be provided as the acidifying agent. In one embodiment, the acidifying agent is aluminum sulfate. In addition, any other suitable acid may be used that does not interfere with the use of the devices as described herein, for example, nitric acid, acetic acid, or sulfuric acid.

It is also appreciated that silver decavanadate in particular may react with sulfide, other halides, and hydroxide to give a positive interference. Advantageously, the present inventor has found that an aluminum-containing compound, such as aluminum sulfate, acts as an interference removal agent, especially in high pH situations, to prevent silver hydroxide formation. Thus, it is appreciated that the carrier matrix 12 may further include an aluminum-containing compound. The aluminum-containing compound may act as an interference removal agent to prevent silver decavanadate from reacting with hydroxide in a high pH sample. In addition, it is contemplated that other interference removal agents selective for sulfide and having greater selectivity for halides other than chloride may be utilized.

When the carrier matrix 12 comprising the indicator 14 is contacted with a chloride ion-containing sample, the chloride ions will react with the silver in the indicator 14 to produce silver chloride. In one embodiment, the indicator 14 comprises silver decavanadate and the reaction with chloride ions takes place according to the following formula:

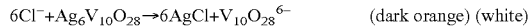

$$6Cl^- + Ag_6V_{10}O_{28} \rightarrow 6AgCl + V_{10}O_{28}^{6-}$$ (dark orange) (white)

The resulting silver chloride product is white, which is easily differentiated from the dark orange silver decavanadate on the carrier matrix 12. In this way also, the silver chloride forms a white peak that is viewable from an exterior of the device 10.

After a sufficient amount of sample has been introduced into the device 10, the amount of chloride in the sample may be determined based upon an empirically derived linear relationship between the extent of silver chloride precipitated and chloride concentrations calculated from a set of chloride standards having various concentrations. The linear regression equation that describes the relationship between the measured chloride concentration in a sample may be derived by analyzing a series of liquid samples each containing a known, different concentration of chloride ion. The observed precipitation areas, e.g., heights, may be measured for each known chloride concentration of the samples. Linear regression analysis may be performed, and the resulting standard curve can be used to calculate the chloride ion concentration in a test sample having an unknown amount of chloride ions. In one embodiment, for example, the height of the visible silver chloride peak may be compared to an associated scale to determine an amount of chloride ions in the sample.

It is generally understood by one skilled in the art that the concentration of the components that form the indicator 14, e.g., the vanadate and silver sources, may be decreased or increased as needed to accommodate the testing of samples having a likely amount of chloride ions. For example, test samples expected to have a relatively high chloride ion concentration will require a larger amount of the indicator 14 in the device 10.

The aforementioned device 10 may be self-supporting, or alternatively may be incorporated within or supported on or by a suitable housing component. It is understood that the construction of the devices having an indicator 14 on a carrier matrix 12 as described herein is not limited to any particular embodiment. Exemplary housing components include those set forth below and those set forth in U.S. Pat. Nos. 6,042,543, 5,229,299, 4,650,768, and 3,620,677, which are incorporated by reference in their entirety herein. In one embodiment, the device 10 comprises a self-supporting carrier matrix is self-supporting and is constructed as depicted in FIG. 1. In another embodiment, the carrier matrix 12 may be disposed on a single backing material. In yet another embodiment, the carrier matrix 12 may be disposed within a housing that partially or wholly encloses the carrier matrix 12. In any of these embodiments, the device 10 may be configured such that the carrier matrix 12 is removable from the housing such that after use of a first carrier matrix 12, a second carrier matrix may be installed in the housing for exposure to a subsequent second test sample.

Figure 2:
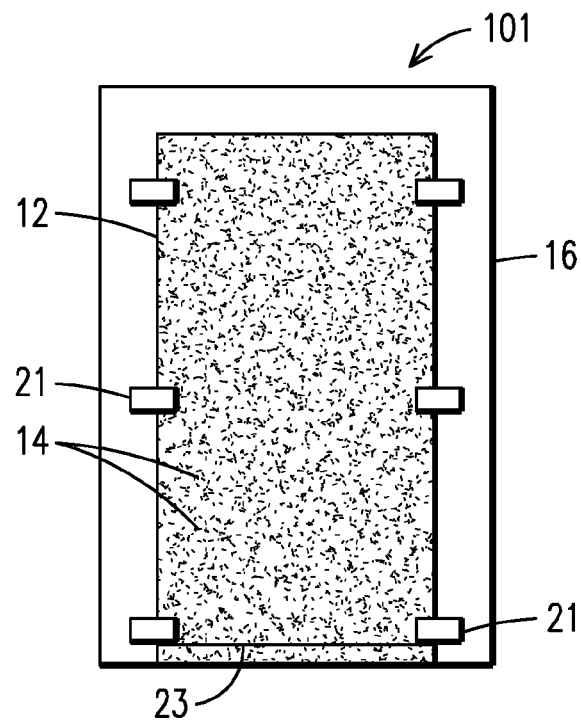
FIG. 2 is a front view of a chemical indicating device supported on a backing strip in accordance with an aspect of the present invention.

FIG. 2 shows another embodiment of an indicating device in accordance with the present invention. The device 101 comprises a housing in the form of a single backing strip 16 for supporting the carrier matrix 12 thereon. The single backing strip 16 is typically formed from a water impermeable material. Suitable water impermeable materials for the backing strip 16 are well known in the art and may include synthetic polymers, including but not limited to polyethylene, polypropylene, polyesters, and the like. In a particular embodiment, the water impermeable material is a biaxially-oriented polyethylene terephthalate (boPET) polyester film commonly sold under the trade name Mylar®. By using a water impermeable material, when the device 101 is inserted in a sample matrix or a sample is otherwise introduced into the device 101, the sample will not be substantially absorbed or fully absorbed by the backing strip 16. The carrier matrix 12 may be fixedly secured to the backing strip 16 via an adhesive or the like, or may be removably secured to the backing strip 16 via any suitable structure, such as tabs 21 or the like. When removably secured to the backing strip 16, it is contemplated that the carrier matrix 12 may be removed from the backing strip 16 after exposure to a first test sample and a new carrier matrix secured to the backing strip 16 for exposure to a subsequent second test sample.

Figure 3:
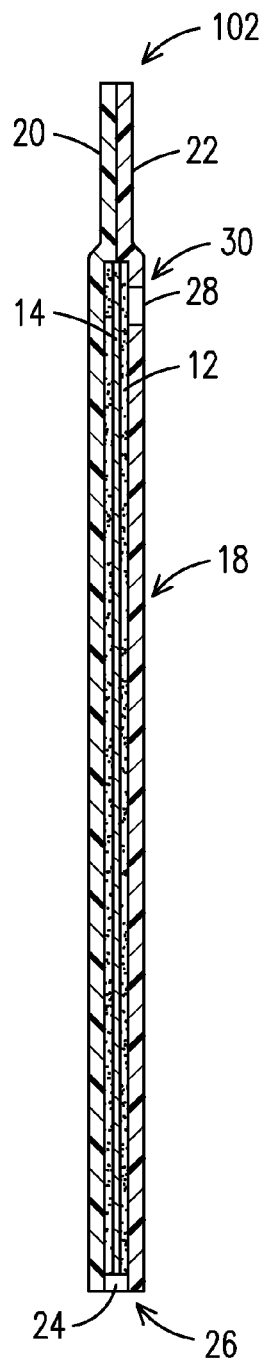
FIG. 3 is a side view of a chemical indicating device disposed within a housing in accordance with an aspect of the present invention.

FIG. 3 shows another embodiment of an indicating device in accordance with the present invention. The device 102 includes a housing 18 comprising an upper backing strip 20 and a lower backing strip 22. The carrier matrix 12 comprises the indicator 14 supported thereon as described previously. In addition, when two backing strips are present, the device 102 typically comprises one or more openings, e.g., opening 24, of any suitable size for allowing a sample to contact the carrier matrix 12. In one embodiment, the opening 24 is defined between the upper backing strip 20 and the lower backing strip 22 at a bottom portion 26 thereof for allowing a sample to contact the carrier matrix 12 as shown. In this way, the sample to be analyzed may be introduced through the bottom portion 26 of the device 102 and may move up the carrier matrix 12 by capillary action. Alternatively, the opening 24 may be disposed at one or more of the outside edges of the device 102, at a center portion of the device 10, or at any other suitable location on the device 102. The upper backing strip 20 and the lower backing strip 22 are preferably formed from a water impermeable material, and in one embodiment, are formed from a substantially translucent or a substantially transparent water impermeable material, e.g., a Mylar® material, such that any change in color of the indicator 14 due to reaction of the indicator 14 with chloride ions in the sample introduced into the device 102 may be easily viewed from an exterior of the device 102.

When the device 102 includes an opening 24 at a bottom portion 26 thereof, the device 102 may further include an opening 28 at an upper portion 30 thereof to act as a vent and to aid the travel of a sample into the opening 24 up the carrier matrix 12 when the device 102 is disposed in a sample matrix. Alternatively, the carrier matrix 12 may extend the entire length of the device to provide an opening at one end thereof, and a second opening acting as a vent at an opposed end thereof. Further alternatively, a plurality holes may be provided in one or more of the upper backing strip 20 and the lower backing strip 22 for venting the device 102.

To produce the device 102 shown in FIG. 3, the carrier matrix 12 can be affixed between the upper backing strip 20 and the lower backing strip 22 by any suitable method. In one embodiment, the upper backing strip 20, lower backing strip 22, and the carrier matrix 12 are arranged together and laminated by the application of pressure and/or heat. In a particular embodiment, the upper backing strip 20, lower backing strip 22, and the carrier matrix 12 are provided in sheet form such that, after lamination, the produced laminated sheet may be cut to produce a plurality of the devices. Alternatively, the carrier matrix 12 comprising the indicator 14 may be cut into strips of a desired length and laminated between sheets of the upper backing strip 20 and the lower backing strip 22 and/or between strips of the upper backing strip 20 and the lower backing strip 22 having substantially the same dimensions. In addition, if a signal string or filter is provided as set forth below, the signal string or filter may be laminated between the upper backing strip 20 and lower backing strip 22 as desired.

Figure 4A:
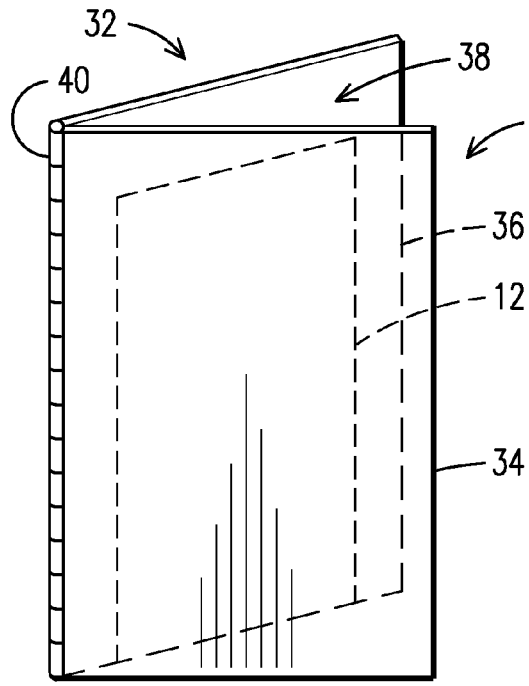
FIGS. 4A and 4B are front views of a reusable chemical indicating device comprising a carrier matrix disposed within a housing that is movable from an open position to a closed position in accordance with an aspect of the present invention.
Figure 4B:
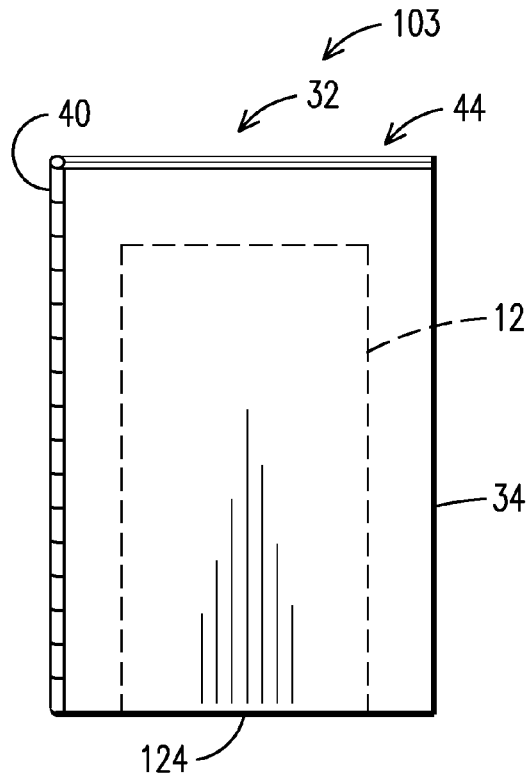

FIGS. 4A-4B show another embodiment of an indicating device in accordance with the present invention. The device 103 comprises a housing 32 comprising a top side 34 and a bottom side 36. The carrier matrix 12 is disposed within a cavity 38 formed between the top side 34 and the bottom side 36. At least one of the top side 34 and the bottom side 36 is movable with respect to the other, such as via a hinge 40, from an open position 42 as shown in FIG. 4A to a closed position 44 as shown in FIG. 4B such that the carrier matrix 12 may be replaced by the user after each test. In this way, a single housing, e.g., housing 32, may be provided with a plurality of carrier matrices for testing a number of samples. Any suitable structure, such as tabs, clasps, or the like, may be provided to secure the carrier matrix in place temporarily within the housing 32 or to hold the top side 34 and the bottom side 36 in a closed position if necessary. When in the closed position 44, the device 103 typically includes one or more openings, e.g., opening 124, defined at a bottom portion of the device 103. Alternatively, the opening may be at any other suitable location and the device 103 may be of any suitable configuration for allowing a single housing to be used with a plurality of replaceable carrier matrices.

Figure 5:
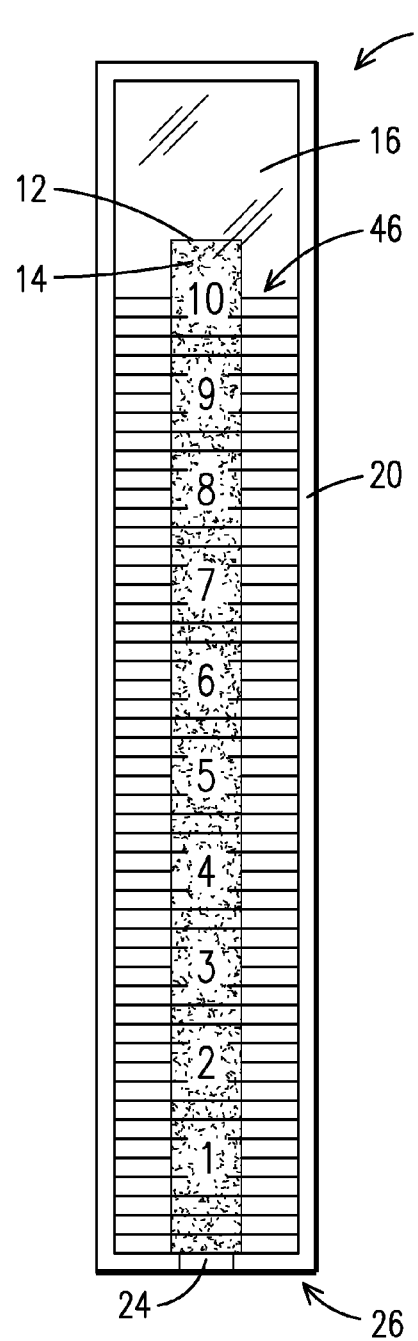
FIG. 5 is a front view of a device having a backing strip with a scale printed thereon in accordance with an aspect of the present invention.

In another aspect of the invention, as shown in FIG. 5, any of the devices described herein may include a backing strip having a scale disposed thereon. FIG. 5 shows the device 102 of FIG. 3, wherein the upper backing strip 20 includes a scale 46 disposed thereon. The scale 46 may have any suitable range and associated markings to accommodate samples having varied concentrations or to accommodate the desired range of the user. The scale 46 may be provided on the upper backing strip 20 (or other backing strip) by any suitable printing or etching method known in the art. In the embodiment shown in FIG. 5, the scale 46 reads from 1 to 10 and allows the user to obtain a scaled value that may be used to determine an amount of chloride ions in the sample by comparison to a chart or a calibration curve derived from the analysis of a series of liquid samples each containing a known, different concentration of chloride ions. In this way, the device 102 provides a measurable colorimetric response to the presence of chloride ions in a sample. In one embodiment, the scale is provided on a substantially translucent or substantially transparent backing strip such that the extent of silver chloride formation from a sample can easily be compared to the scale 46.

Figure 6:
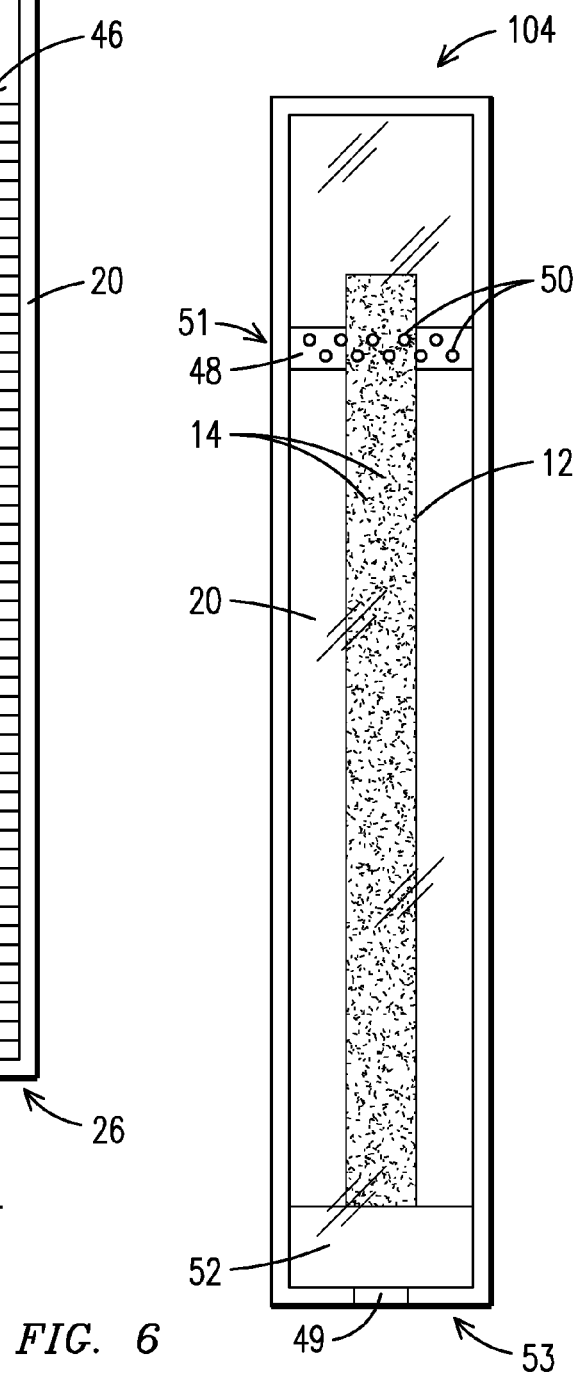
FIG. 6 is a rear view of a chemical indicating device in accordance with an aspect of the present invention.

In an alternate embodiment to the one depicted in FIG. 5, a scale similar to the one depicted in FIG. 5 may be provided as a separate component from the device 10 and placed adjacent the produced white silver chloride peak (if present) to determine the scaled value. For example, the separate component comprising a scale may be a strip of a substantially translucent or a substantially transparent material having the scale printed thereon. A calibration curve may be provided with the device 10 and a separate scale that correlates the scaled value to a predetermined amount of chloride ions in the test sample. In the manufacturing of the device 10, it is understood that each production lot of paper may have its own calibration curve. In accordance with another aspect of the present invention, any embodiment of the devices as described herein may comprise a signal string 48 as shown in FIG. 6. As shown in FIG. 6, the device 104 comprises a signal string 48 disposed at the upper portion 49 of the device 104 to provide an indication of the completion of the titration. In other words, the signal string 48 provides an indication that a sample has moved from a starting point, e.g., the opening 49, to the location of the signal string 48. When the sample reaches the signal string 48, the testing is substantially to fully complete. Holes 50 may further be provided on an upper portion 51 of the device 104 (e.g., on one of the backing strips) where the signal string 48 is disposed to act as a vent to allow air to escape as a sample enters the device 104, e.g., through the opening 49 of the bottom portion 53 of the device 104. In one embodiment, the signal string 48 is impregnated with a dye that is responsive to an aqueous fluid.

In accordance with another aspect of the present invention, the device 104 may further include a filter 52 as shown in FIG. 6 for preventing particulate matter from entering the device and for reducing or eliminating pH interference for the indicator 14. The indicator 14 may be subject to high pH interference (e.g., pH>10). In some cases, for example, the pH of the sample may be as high as 12-13. This is generally the case with cement samples. With such high pH samples, it may be desirable to incorporate the filter 52 into the device 104 in any suitable location where the filter 52 will contact the sample prior to the sample entering the device 104 or thereafter to lower the pH of the sample. In one embodiment, the filter 52 is disposed adjacent the opening 49, e.g., within, forward of, or behind the opening 49, such that a sample entering the device contacts the filter prior to contacting the indicator 14.

The filter 52 may comprise any suitable laboratory grade filter paper known in the art, such as those available from Whatman, Inc. To eliminate pH interference, the filter 52 may be pretreated with a component that will generate a plurality of anions that will not interfere with the determination of chloride in the sample. In one embodiment, the filter 52 is pre-treated with a suitable acidic compound such as zinc nitrate or magnesium sulfate. In another embodiment, the filter 52 is pre-treated with aluminum sulfate, which will provide sulfate ions in the presence of water. In one embodiment, the treated filter 52 is effective to modify the pH of any sample passing through the filter 52 to a pH of 3-6, which is the optimum pH for the indicator 14. As mentioned above, the filter 52 also has the added benefit of removing particulate matter that might clog or otherwise interfere with the normal operation of the device 10. With the filter 52, a further variety of samples, including cement samples, may be optimally tested using the device 10.

The above-description discussed the use of the devices for the detection of chloride ions. It is understood, however, that any embodiment of the devices described herein may also react with sulfide and other halides beside chloride. Thus, if desired, the device 10 may be utilized in a similar manner as described above to detect the presence of other halides in a sample, as well as sulfide.

It is generally understood that when a sample suspected of having chloride ions is introduced into a bottom portion of any embodiment of the devices described herein that it is desirable that the sample only contact a bottom edge of the carrier matrix 12, or up to a height slightly above the bottom edge of the carrier matrix 12. For example, in the embodiment shown in FIG. 1 and in the case of a hydrophilic carrier matrix 12, it is desirable to contact the bottom edge of the carrier matrix 12 with the sample to an extent sufficient for the sample to passively move up the carrier matrix 12. Optionally, any suitable indicia may used or provided to inform the user that the carrier matrix 12 of the device should not be immersed in the test sample beyond a certain depth. These indicia may include a horizontal line 21 across the carrier matrix as shown in FIG. 2, or may be any suitable component that can serve as a marking, such as the lowermost tabs of tabs 21 as is also shown in FIG. 2. In the embodiment of FIG. 3, the upper backing strip 20 and the lower backing strip 22 inherently allow the sample to be introduced only at a bottom edge of the carrier matrix.

Figure 7:
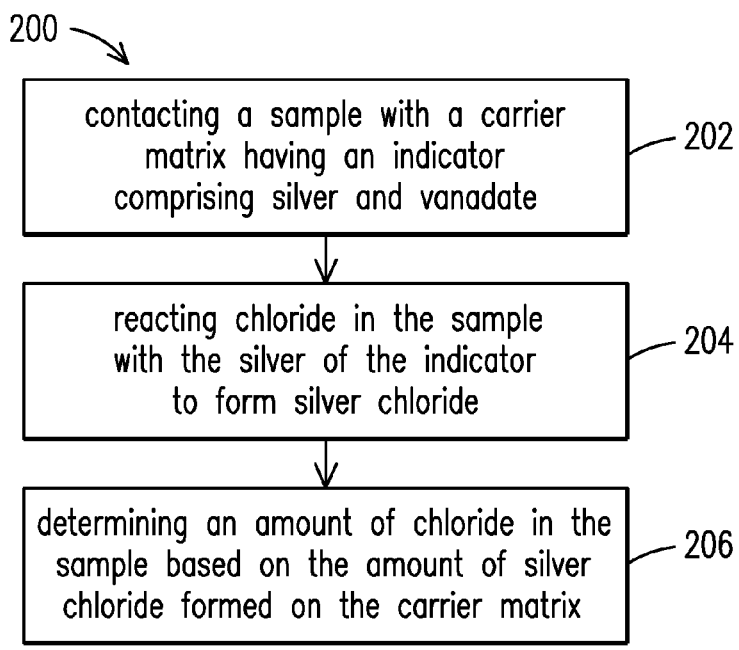
FIG. 7 is a flow diagram showing a method in accordance with an aspect of the present invention.

Referring to FIG. 7, there is shown a method 200 for detecting chloride in a sample using the above-described device 10. The method 200 comprises step 202 of contacting a sample suspected of having chloride ions with a carrier matrix 12 having an indicator 14 comprising silver and vanadate supported on the carrier matrix 12. In addition, the method comprises step 204 of reacting the chloride in the sample with the silver of the indicator 14 to form an amount of silver chloride along a length of the carrier matrix 12. Further, the method comprises step 206 of determining an amount of chloride in the sample based upon the amount of the silver chloride formed along the length of the carrier matrix 12. It is understood that the sample may move over at least a portion of the carrier matrix 12 by passive (e.g., capillary) or active (e.g., via syringe) methods. As used herein, the length of the carrier matrix 12 implies a distance in any direction of the carrier matrix 12.

The amount of silver chloride formed along the length of the carrier matrix may be referred to as the indication length. When, for example, the sample enters the device at a bottom portion 26 of the device 102 as shown in FIG. 3, for example, the sample may flow via capillary action along a length of the carrier matrix to an upper portion of the carrier matrix. This indication length may be characterized as the height of silver chloride formation. Alternatively, if the sample is introduced into an interior, e.g., center portion, of the device, e.g., device 102, and flows radially outward in the form of a circle, the indication length along which the silver chloride forms may be characterized as the radius or diameter of the circle where silver chloride is precipitated. In one particular embodiment, the step 106 of determining comprises comparing the amount of silver chloride formed along the length of the carrier matrix 12 (e.g., the indication length) to values of a calibration curve created from a plurality of standard samples having predetermined chloride concentrations.

Aspects of the present invention are demonstrated by the following examples, which are not intended to be limiting in any manner.

Example 1

This example illustrates the manufacture of a chemical indicating device in accordance with the present invention. An impregnated matrix of cellulose paper was prepared in a two dip process utilizing a cellulose paper provided from Whatman, Inc. The first dip solution contained deionized (DI) water, silver nitrate, and ethanol in the following quantities:

| Solution 1 | |
|---|---|
| DI water | 900 mL |
| Silver Nitrate | 5.20 grams |
| SDA Ethanol (200 proof) | 100 mL |

After dipping the cellulose paper in Solution 1 to produce a first dipped matrix, the first dip matrix was dried and rolled such that the first dipped matrix could be dipped into a second solution. Generally, the cellulose paper becomes saturated very quickly.

The second solution contained deionized water, potassium metavanadate, aluminum sulfate, and ethanol in the following quantities.

| Solution 2 | |
|---|---|
| DI water | 800 mL |
| Potassium metavanadate | 10 grams |
| Aluminum sulfate | 30 grams |
| SDA Ethanol (200 proof) | 200 mL |

The silver from Solution 1 reacted with the decavanadate ions formed in Solution 2 to produce an orange colored precipitate, namely silver decavanadate, which was impregnated within the cellulose paper. The cellulose paper was then dried. The finished dried paper was then slit into 2.6" strips widths, and then again in ⅕" widths. Thereafter, the finished dried strips were laminated between two strips of a Mylar® material of approximately the same size to produce the device. An opening in the device was created by purposefully not allowing a bottom portion of the two strips of a Mylar® material to be laminated together. The finished device was then tested by placing the device in a sample comprising 100 ppm of chloride ions. In this example, the 5.2 grams of silver nitrate produces a device that may detect chloride in 0% to 0.5% NaCl solutions. The chloride ions in the sample reacted with the produced silver vanadium oxides on the cellulose paper to create a white peak of a particular height. The white peak was then compared to an arbitrary scale located on one of the Mylar® strips and the concentration was determined from an associated calibration graph.

Example 2

This example illustrates the manufacture of another chemical indicating device in accordance with the present invention. An impregnated matrix of cellulose paper was prepared in a two dip process utilizing a cellulose paper provided from Whatman, Inc. The first dip solution contained 5.2 grams of silver nitrate, 900 mL of DI water, 100 mL of ethyl alcohol, and 28 grams of aluminum nitrate. After dipping the cellulose paper in Solution 1 to produce a first dipped matrix, the first dip matrix was dried and rolled such that the first dipped matrix could be dipped into a second solution.

The second solution contained 800 mL of DI water, 9.6 grams of ammonium metavanadate, 5.0 mL of acetic acid, and 200 mL of ethyl alcohol. The silver from Solution 1 reacted with the vanadate from Solution 2 to produce an orange colored precipitate, namely silver decavanadate, which was impregnated within the cellulose paper. The cellulose paper was then dried and a finished device was formed and used as was described above in Example 1.

Example 3

Figure 8:
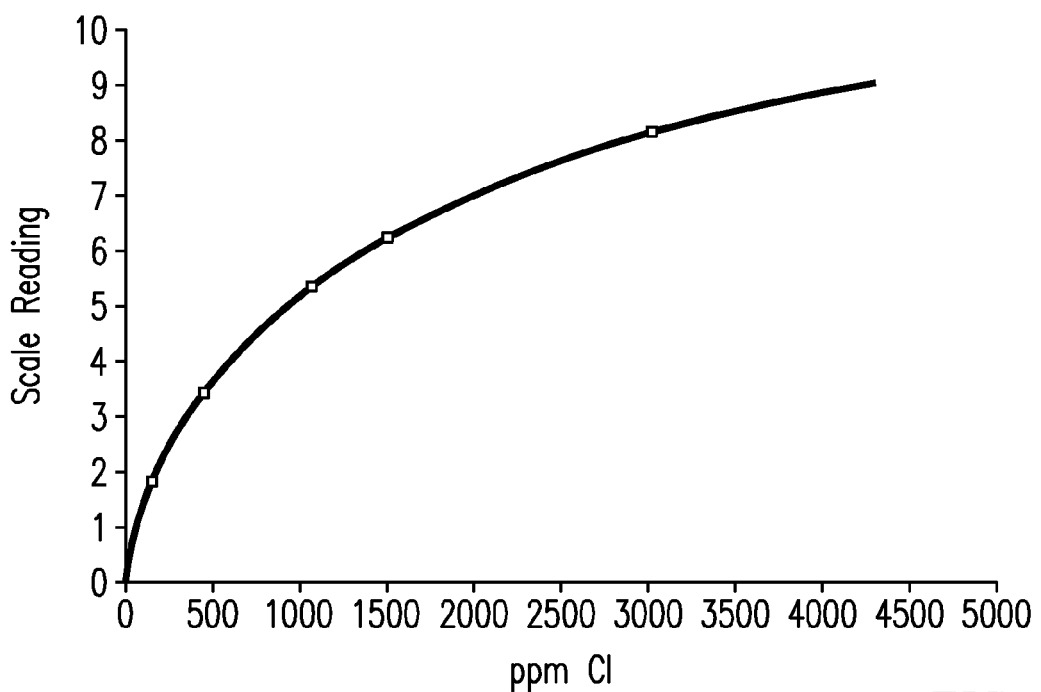
FIG. 8 represents a calibration curve for determining an unknown concentration of chloride in a sample in accordance with an aspect of the present invention.

Using the device manufactured in Example 1 above, the preparation of a calibration curve to determine an amount of chloride in an unknown sample was established. A set of standards ranging from 0-3500 ppm of chloride was used to build a scale ranging from 0-10 units as shown on the Y axis of the figure in FIG. 8 and in Table 1. This scale may be provided on a strip overlaying the carrier matrix of the device or may be provided as a separate component. Utilizing five (5) selected standards set forth below, a calibration curve was then established for determining an unknown concentration of chloride ions. Error bars for each standard are also depicted in FIG. 8. By obtaining the scale reading of the unknown sample, the amount of chloride in the sample make be easily determined by reference to the Y axis and t X axis in the curve of FIG. 8.

TABLE 1

| NaCl ppm | Scale Units | $+x_{err}$ | $-x_{err}$ | $+y_{err}$ | $-y_{err}$ |
|---|---|---|---|---|---|
| 0 | 0 | | | | |
| 152 | 1.8 | 1.4 | 1.4 | 0.0178 | 0.0178 |
| 453 | 3.4 | 17 | 17 | 0.0706 | 0.0706 |
| 1070 | 5.3 | 36 | 36 | 0.085 | 0.085 |
| 1506 | 6.2 | 56 | 56 | 0.1003 | 0.1003 |
| 3023 | 8.1 | 68 | 68 | 0.0598 | 0.0598 |

While various embodiments of the present invention have been shown and described herein, it will be obvious that such embodiments are provided by way of example only. Numerous variations, changes and substitutions may be made without departing from the invention herein. Accordingly, it is intended that the invention be limited only by the spirit and scope of the appended claims.

The invention claimed is:

1. A chemical indicating device for detection of chloride ions in a sample comprising:
   a carrier matrix;
   an indicator comprising silver and vanadate supported by the carrier matrix for exposure to the sample.

2. The chemical indicating device of claim 1, wherein the vanadate comprises decavanadate, and wherein the indicator comprises silver decavanadate.

3. The chemical indicating device of claim 1, wherein the carrier matrix comprises at least one of a cellulosic material, a glass fiber material, or a porous polymer material.

4. The chemical indicating device of claim 1, wherein the carrier matrix is disposed within a housing, and wherein the housing is configured to move from an open position to a closed position about the carrier matrix for allowing replacement of the carrier matrix within the housing.

5. The chemical indicating device of claim 1, wherein the carrier matrix is disposed on a single backing strip.

6. The chemical indicating device of claim 1, wherein the carrier matrix is disposed within a housing having an upper backing strip and a lower backing strip, and wherein the device further comprises an opening in the housing for allowing the sample to enter the device and contact the indicator.

7. The chemical indicating device of claim 6, wherein at least one of the upper backing strip and the lower backing strip is formed from a substantially translucent or a substantially transparent material.

8. The chemical indicating device of claim 6, further comprising a filter disposed adjacent the opening for filtering the sample upon entry into the device, wherein the filter is pretreated with at least one of zinc nitrate, magnesium sulfate, or aluminum sulfate.

9. The chemical indicating device of claim 1, further comprising an aluminum compound supported by the carrier matrix.

10. The chemical indicating device of claim 1, wherein the indicator is evenly distributed on the carrier matrix, and wherein the indicator is substantially immobilized on the carrier matrix.

11. The chemical indicating device of claim 1, wherein the device is free of chromium.

12. A method for detecting chloride in a sample comprising:
    contacting a sample suspected of having chloride ions with a carrier matrix having an indicator comprising silver and vanadate supported on the carrier matrix;
    reacting the chloride in the sample with the silver of the indicator to form an amount of silver chloride along a length of the carrier matrix;
    determining an amount of chloride in the sample based upon the amount of the silver chloride formed along the length of the carrier matrix.

13. The method of claim 11, wherein the vanadate comprises decavanadate, and wherein the indicator comprises silver decavanadate.

14. The method of claim 11, wherein the silver is provided by a silver source, and wherein the vanadate is provided by a vanadate source, and wherein the indicator comprises silver decavanadate formed from a reaction between the silver source and the vanadate source.

15. The method of claim 14, wherein the vanadate source comprises at least one of metavanadate, orthovanadate, or vanadium oxide.

16. The method of claim 14, wherein the vandate comprises decavanadate, and wherein the decavanadate is provided from the vanadate source by adjusting a pH of the vanadate source to a pH of between 3 and 6 to provide the decavanadate.

17. The method of claim 14, further comprising preparing the indicator by contacting the carrier matrix with the silver source and the vanadate source, wherein a mole ratio of vanadium to silver is at least 2:1.

18. The method of claim 14, further comprising adding an aluminum-containing compound to at least one of the silver source or the vanadate source to act as an interference removing agent.

19. The method of claim 12, wherein the indicator is formed by first dipping the carrier matrix in a first solution comprising silver nitrate to provide a first dipped matrix and subsequently dipping the first dipped matrix in a second solution comprising decavanadate to provide a second dipped matrix.

20. The method of claim 12, wherein the indicator is maintained free of chromium.

21. The method of claim 12, wherein said determining comprises comparing an amount of chloride formed along the length of the carrier matrix to values of a calibration curve created from a plurality of standard samples having predetermined chloride concentrations.

* * * * *